United States Patent
Gadkaree et al.

(10) Patent No.: US 6,455,023 B1
(45) Date of Patent: Sep. 24, 2002

(54) METALLIC CATALYSTS FOR NON-NEUTRAL LIQUID MEDIA

(75) Inventors: Kishor P. Gadkaree; Tinghong Tao, both of Big Flats, NY (US)

(73) Assignee: Corning Incorporated, Corning, NY (US)

( * ) Notice: Subject to any disclaimer, the term of this patent is extended or adjusted under 35 U.S.C. 154(b) by 16 days.

(21) Appl. No.: 09/686,555

(22) Filed: Oct. 11, 2000

(51) Int. Cl.[7] .............................. C07C 5/00; C07C 5/05; C07C 5/02; C07C 27/04; C10G 45/04
(52) U.S. Cl. ...................... 423/659; 208/213; 208/217; 208/254 H; 208/262.1; 540/540; 560/241; 562/519; 564/261; 564/312; 564/415; 564/420; 568/885; 585/250; 585/271; 585/273; 585/274; 585/275; 585/276
(58) Field of Search .................. 423/659, 213, 423/217; 208/254 H, 262.1; 540/540; 560/241; 562/519; 564/415, 420, 261, 312; 568/885; 585/250, 271, 273, 274, 275, 276

(56) References Cited

U.S. PATENT DOCUMENTS

| | | | | |
|---|---|---|---|---|
| 5,332,496 A | * | 7/1994 | Rasouli et al. | 210/180 |
| 5,451,444 A | | 9/1995 | DeLiso et al. | |
| 5,487,917 A | | 1/1996 | Gadkaree | |
| 5,488,023 A | | 1/1996 | Gadkaree et al. | |
| 5,637,286 A | * | 6/1997 | Turunen | 423/588 |
| 5,998,328 A | | 12/1999 | Dawes et al. | |

* cited by examiner

*Primary Examiner*—Wayne A. Langel
(74) *Attorney, Agent, or Firm*—Kees van der Sterre

(57) ABSTRACT

Carbon monolith-supported catalysts with high leach resistance used in catalytic applications involving strong acidic and basic conditions in a pH range of from 0 to 6.5 and from 7.5 to 14, are respectively described. The leach resistance of the catalyst system originates from strong interaction between the catalyst and the unsaturated valence of the carbon surface. In addition to surprisingly high resistance to leach out, the catalysts also have substantial differential advantages in catalyst performance: catalyst activity, selectivity, and stability.

10 Claims, No Drawings

METALLIC CATALYSTS FOR NON-NEUTRAL LIQUID MEDIA

BACKGROUND OF THE INVENTION

The present invention relates to metallic catalysts, and more particularly to metallic catalysts that promote catalytic reactions in a non-neutral pH liquid environment, with high leaching resistance, and the use thereof to promote chemical reactions in non-neutral liquid media.

Activated carbon has high chemical resistance in most inorganic and organic solutions. This is particularly so in acidic conditions. Other materials like alumina, silica, zeolite, and aluminosilicates, etc., do not fare as well.

This unique attribute of activated carbon has resulted in its commercial use as a catalyst support in non-neutral pH conditions. It has been found, however, that catalysts supported upon activated carbon surfaces are not retained on the surface of carbon during process under non-neutral pH conditions. This leaching phenomenon becomes a major concern in commercial use of these carbon-supported catalysts.

This commercial catalyst leachout problem is associated with a relatively weak chemical interaction between the carbon surface of the support and the catalyst. This has become a serious problem for the industry, of course, because catalyst leachout shortens the useful life of the catalyst and its productivity.

Therefore, a need has developed to provide an improved, activated, carbon-supported catalyst with resistance to leaching in non-neutral pH environments.

SUMMARY OF THE INVENTION

We have now discovered that metallic catalysts supported on porous, inorganic supports consisting of activated carbon-coated honeycombs of the type illustrated in U.S. Pat. Nos. 5,451,444 and 5,488,023 exhibit a surprising resistance to catalyst loss in both high and low pH reaction media. The present invention accordingly features a new family of carbon monolith-supported catalysts having substantially better stability in non-neutral pH solutions than previously obtained from commercially activated carbon-supported catalysts. This new family of carbon supported catalysts provides better catalytic performance, selectivity, and active lifetimes than prior art catalysts.

Therefore, in accordance with the present invention there is provided a method for promoting a catalytic reaction by contacting a liquid reactant mixture of non-neutral pH with a metallic catalyst supported by a solid inorganic support. The support includes a solid inorganic honeycomb substrate having surfaces with pores extending into the substrate, and incorporates a substantially uninterrupted adherent layer of activated carbon over the pore surfaces and an outer surface of the substrate. The metallic catalyst is supported upon, and/or dispersed throughout the adherent layer of activated carbon.

DETAILED DESCRIPTION

Generally speaking, the invention features carbon monolith-supported catalysts with high leaching resistance in catalytic chemical processes involving both strong acidic or basic conditions. The catalyst is formulated by loading the catalyst compositions onto carbon monolith supports using impregnation, precipitation, chemical vapor deposition, ion exchange, in-situ technology, and other techniques known in the art. These supported catalysts have surprisingly high resistance against leaching from their supports. The catalysts also have substantial differential advantages in catalyst performance: catalyst activity, selectivity, and stability in various reactions, as will be described hereinafter, particularly in comparison with commercially available, activated carbon supports and other inorganic supported catalysts.

Carbon monoliths are carbon impregnated honeycombs (CiHs) and extruded resin carbon honeycombs (ERCHs), illustrated in the aforementioned U.S. Pat. Nos. 5,451,444 and 5,488,023. These carbon monoliths are subjected to physical and chemical modifications to make their surface suitable for catalyst loading and to enhance their performance in practical applications. The modifications can be made through their composition formulations or through surface modifications after carbon formation. Depending upon the application, the carbon monoliths can be tailored so that their pore size range is in the micropore, mesopore, or macropore range, each with a desired pore size distribution. Mesopores are favored, when a chemical reaction is limited by a mass transfer step. On the other hand, when a reaction is governed by reaction kinetics, micropores are desirable. Carbon loading in a carbon monolith is usually in the range of between 5% to 99%. Pore volume and surface area are usually in the range of 0.1 to 1.4 ml/g C, and 10–3000 m$^2$/g C, respectively.

Depending upon the catalyst, its composition, and the desired application, the preparation of the catalyst support will vary. For example, a Pt/CIH catalyst can be prepared using liquid solution impregnation and in-situ approaches; Ni/CIH can be prepared using co-precipitation and chemical vapor deposition. However, catalyst quality is measured by catalyst performance in a targeted application and its acidic or basic resistance, and/or leaching resistance, in solution.

Catalysts that are used for catalytic reactions in acidic or basic solution comprise precious group metals (Pt, Pd, Rh, Ru, Ir, Ag, Os and Re) and transitional metals (Fe, Co, Ni, Cu, Mo, Au, Cr, and Zn) and their compounds.

Catalysts additionally used for catalytic reactions in basic solution are alkali and alkaline metals (K, Na, Li and Mg, Ca, Ba, Ra), rare earth metals (La, Ce, Pr, Yb, and Ac) and their compounds.

Depending upon individual applications, some additives are needed, such as electron factor promoters and/or geometric factor promoters and/or carbon stabilizers. These additives enhance catalyst activity, selectivity, stability, lifetime, etc.

Electron factor promoters include alkali-metals and compounds, group IB metals and compounds, etc. Due to electron exchange capability with d-orbits in main catalysts, the promoters enhance main catalyst performance. Geometric factor promoters comprise alkali earth metals and compounds, rare earth metals and compounds, co-existing transitional metals and compounds thereof, etc.

These promoters are able to interact physically with the main catalyst, to keep catalyst particles apart during chemical processes. Thus, they maintain high surface area of the catalysts, and hence, high effective catalyst usage.

Carbon stabilizers include non-metal compounds like boron, silicon, phosphorous, sulfur, selenium, arsenic, and even oxygen, etc. Most carbon stabilizers can react with highly active carbon sites, in order to saturate carbon surfaces. Hence, they provide deactivation protection for the catalysts during storage and transportation.

The present invention features a new family of carbon monolith-supported catalysts. The unique family of carbon monolith-supported catalysts have substantial differential advantages in reactor design and operation, mass and heat transfer, intrinsic reaction kinetics, and catalyst performance, over commercially available, activated carbon and other supported catalysts in various industrial reactions. In particular, reactions carried out under acidic conditions are most significant as illustrated below:

1. Hydrogenation of nitrites and nitro-aromatics into amines are carried out in acidic solvent over carbon-supported precious metal catalysts. Acidic solvent in the reaction system has an additional promotion function to the main catalyst.

2. Purification of ε-caprolactam (nylon-6 precursor) by selectively hydrogenating olefinic impurities at a 10 to 50 ppm level is conducted in a strong acidic (pH=1 to 6) condition, originating from synthesis of ε-caprolactam in one of three strong acids (sulfuric acid, nitric acid, and hydrochloric acid), depending upon the process.

3. Hydrogenation of aromatic and paraffinic aldehydes, ketones, and acids into their corresponding alcohols is performed in acidic solvents to prevent hydrogenolysis and to promote catalyst performance.

4. Acidic solvents are often used to promote the reaction or prevent side reactions in hydrogenation of other organic compounds containing unsaturated double bonds of C=C, C=O, C=N, and N=O, unsaturated triple bonds of C≡C, C≡N, aromatic rings, and benzyl compounds, etc.

5. Acetoxylation of olefins and toluene into their corresponding acetates is favored, when conducted in hydrochloric acid over promoted precious metal catalysts in a temperature range of approximately 25 to 200° C.

6. Carbonylation of methanol to acetic acid and its derivatives involves the highly corrosive solvent $CH_3I$, and causes leaching of catalyst from catalyst supports. This is one of the key issues related to the practicality of heterogeneous catalysis for methanol carbonylations. In most of hydrogenolysis reactions, acidic solvent can promote catalytic performance over carbon-supported precious metal catalysts.

Commercial activated carbon and other supported catalysts in various industrial basic reactions are:

1. Purification of ε-caprolactam (nylon-6 precursor) by selectively hydrogenating olefinic impurities at a 10–50 ppm level is conducted in a strong basic (pH=7.5 to 14) condition originated from neutralization of one of three strong acids after synthesis of ε-caprolactam.

2. Hydrogenation of nitroaromatic compounds to hydrazobenzenes is more effective when the reaction is carried out in organic and inorganic base media over supported precious metal catalysts in a temperature range from ambient to 100° C.

3. Dehydrohalogenation of aliphatic and aromatic halo-compounds into their corresponding non-halogenated hydrocarbons is more selective in basic solvents, since the formed by-product, hydrohalogenic acid, can be removed easily in the reaction through acid-base reaction with a reaction solvent.

4. Selective hydrogenations of nitro-olefins to oximes are more effective over supported Pd catalysts, when basic solvents like pyridine are used.

In addition, it is believed that the catalysts and catalyst supports of this invention can be advantageous, when used in the following catalytic reactions:

a) hydrogenation of alkynes into olefins, olefins into alkanes, ketones and aldehydes into alcohols, aromatics into cycloparaffins, fatty oil purifications, etc.; and b) hydrotreating crude oils to remove sulfur (hydrodesulfurization, HDS), nitrogen (hydrodenitrogenation, HDN), and halogen (hydrodehalogenation, HDX); carbonylation of methanol to acetic acid and its derivatives.

The invention may be further understood by reference to the following detailed examples which are, however, intended to be illustrative rather than limiting.

EXAMPLE I

A 1% Pt/carbon-supported commercial catalyst (1% Pt/C about 10 mesh in particle size) was provided in dried base, having a surface area of 800 $m^2/g$, and pore volume of 0.6 cc/g. After grinding the Pt/C catalyst into a powder form (−200 mesh), the Pt/C catalyst was placed in pH=1, HCl aqueous solution (solution to solid catalyst ratio of 40:1 ml/g) for 24 hours at 60° C., while stirring continuously. After the leaching experiment, the solution was separated from the solid catalyst, and then analyzed using plasma ICP-MS for Pt concentration. It was found that the concentration of Pt in the leaching solution was 21.6 μg Pt/mL. This indicated that about 8.6% of the total amount of Pt on the catalyst was dissolved in the acidic solution. The result indicates that the commercial activated carbon-supported Pt/C catalyst is not stable. The low stability of the commercial Pt/C catalyst is probably due to weak chemical interaction between the Pt and the carbon surface resulting from the catalyst preparation process.

EXAMPLE II

A 1% $Pt/Al_2O_3$-supported commercial catalyst (1% $Pt/Al_2O_3$, and about 10 mesh in particle size) was provided, having a surface area of 200 $m^2/g$ and pore volume of 0.6 cc/g. The acid leaching experiment was carried out under conditions described in Example I. The Pt concentration in the leaching solution was 172 μg Pt/mL. Again, about 50% of the total amount of Pt on the carbon support was dissolved in the acidic solution.

EXAMPLE III

Carbon impregnated honeycombs (CIH carbons) were fabricated according to the method described in U.S. Pat. No. 5,451,444. For the catalyst support application, the CIH carbon was carefully optimized in the processes of carbonization and activation to develop its surface physical and chemical properties, including surface area, pore volume and pore size. The CIH carbons were impregnated with a Pt precursor using an incipient wetness impregnation method. Dihydrogen hexachloroplanitic acid was used as a Pt precursor. Approximately 1 wt. % of Pt was directly loaded into the CIH carbon without further treatment (i.e., Pt to carbon weight ratio of 0.01). The sample was dried overnight in air at 120° C. After being calcined at 400° C. for 2 hours in inert gases, the sample was cooled to room temperature and stored in air for future use. The Pt/C ratio of 0.01 was thus identical to commercial Pt/C catalysts in Examples I and II.

The Pt/C ratio is a primary factor in determining Pt dispersion and chemical contact on carbon. The inventive carbon monolith-supported Pt catalyst of Pt/CIH was ground into powders with the same range of particle size as the commercial sample in Examples I and II, and leached under the conditions described in Examples I and II. The reason for grinding carbon monolith-supported Pt catalysts into powder was to eliminate possible physical shape effect on acidic leaching results. The result showed that there was 0.06 μg Pt/mL in the leaching solution. This indicated that there was very little Pt leachout in the acid solution for the carbon monolith supported Pt/CIH catalyst. This result clearly demonstrates that the Pt was attached in a more stable manner to carbon. This surprisingly good Pt stability probably results from strong chemical interaction between Pt and the carbon monolith surface introduced in catalyst preparation.

For comparison, the integrated monolith Pt/CIH catalyst, without further grinding, was also studied. It was found that the Pt stability was similar to that of powdered samples.

EXAMPLE IV

In-situ carbon monolith-supported (in-situ Pt/C) catalysts were fabricated according to the method described in U.S. Pat. No. 5,488,023. Approximately 1 wt. % of Pt was loaded into the carbon in the monolith. The Pt to carbon weight ratio was 0.01. The inventive in-situ carbon monolith-supported Pt catalyst of Pt/C was ground into powders with the same particle size range as the commercial sample in Examples I through m, and then leached under the conditions described in these Examples. The result showed that there are 0.11 μg Pt/mL existing in solution for the in-situ Pt/C catalyst. This indicated that there is little Pt being dissolved in the acid solution for the in-situ Pt/C catalyst, similar to that of the Pt/CIH catalyst found in Example III. It again suggested that the in-situ Pt/C catalyst is also much more stable in Pt on the carbon surface than are the commercial counterparts of Pt/C and Pt/$Al_2O_3$ described in Examples I and II. It is believed that intimate and strong chemical interaction between Pt and the carbon surface was introduced in catalyst preparation, since the Pt catalyst was incorporated into the carbon body in the beginning of the process. It is surprising to note that the in-situ Pt/C catalyst has very similar Pt leaching stability to the Pt/CIH catalyst described in Example III. For comparison, the integrated, monolithic, in-situ Pt/C catalyst was also studied, and the obtained result of Pt stability is similar to that of powdered samples.

The following examples show that the strongly leaching resistant catalysts described in inventive Examples III and IV above also have significantly better catalyst performance under standard reaction conditions compared to commercial, carbon-supported catalysts.

EXAMPLE V

A commercial, 1.7 g., 1% Pt/carbon-supported catalyst as previously described was mixed after grinding into powder form (–40 mesh), with about 7.2 g of 2040 mesh corderite (total sample volume of 12.87 cc), and was charged to a 1" internal diameter reactor. Since the sample was supplied in a pre-reduced form, the sample was retrieved at 150° C., in flowing 10% $H_2/N_2$ at 1,000 cc/min for 1 hour. The sample was cooled rapidly to 25° C. in the 10% $H_2/N_2$ atmosphere. After the catalyst temperature was stabilized, the cyclohexene feed rate was adjusted to give a contact time of 4.2 hours. (For example, a cyclohexene feed rate of 0.05 cc/min gives a reaction or contact time of 4.2 hours.) The total gas flow rate of 10% H2/N2 mixture was adjusted to give a hydrogen space-time of 0.53 second.

The hydrogenation reaction was carried out at a reaction temperature of 25° C. The reaction product was sampled continuously using a six-port, gas phase, automatic sampling valve. The reaction product distribution was an average of several measurements taken after steady-state conditions were reached. The reaction was continuously conducted for 72 hours. The conversion of cyclohexene to cyclohexane was 51.0% in the beginning of testing, and decreased to 24.2% at the end. This was about a 52.5% loss of the original catalyst activity during the 72 hour testing period.

EXAMPLE VI

In-situ, carbon monolith-supported (in-situ Pt/C) catalyst, described in Example IV, was fabricated according to the method described in U.S. Pat. No. 5,488,023. Approximately 1 wt. % of Pt was loaded into the carbon in monolith. The Pt to carbon weight ratio was 0.01. The sample was continuously tested for 72 hours under the conditions described in Examples IV and V. The testing resulted in a conversion of cyclohexene to cyclohexane of 82.1% in the beginning of testing, and 72.8% at the end. This was only about an 11.3% loss of the original catalyst activity during the 72 hour testing period. Compared to 52.5% loss of activity over commercial Pt/C catalyst in Example V, the inventive, in-situ Pt/C catalyst was about 4.6 times better in catalyst stability in a representative reaction of cyclohexene hydrogenation at 25° C.

EXAMPLE VII

A 1% Pt/carbon-supported commercial catalyst (1% Pt/C and about 10 mesh in particle size) was provided in dried base, having a surface area of 800 $m^2$/g, and a pore volume of 0.6 cc/g. After grinding into powder form (–200 mesh), the Pt/C catalyst was placed in pH=12.84 KOH aqueous solution (solution to solid catalyst ratio of 40:1 ml/g) for 24 hours at 60° C., while continuously stirring. After leaching, the solution was separated from the solid catalyst and then analyzed using plasma ICP-MS for Pt concentration. It was found that the Pt concentration in the leaching solution was 14 μg Pt/mL. This indicated that about 5.6% of the total amount of Pt on the catalyst was dissolved in the basic solution. The result indicated that the commercial, activated carbon-supported Pt/C catalyst is not stable. The low stability of the commercial Pt/C catalyst is probably due to weak chemical interaction between Pt and the carbon surface resulting from catalyst preparation process.

EXAMPLE VIII

A 1% Pt/$Al_2O_3$-supported commercial catalyst (1% Pt/$Al_2O_3$, about 10 mesh in particle size) was provided, having a surface area of 200 $m^2$/g and a pore volume of 0.6 cc/g. The base leaching experiment was carried out under conditions described in Example VII. The Pt concentration in the leaching solution was 21 μg Pt/mL. Again, about 8.6% of the total amount of Pt on the carbon support was dissolved in the basic solution.

EXAMPLE IX

Carbon impregnated honeycombs (CIH carbons) were fabricated according to the method described in U.S. Pat. No. 5,451,444. For catalyst support application, the CIH carbon was carefully optimized in the processes of carbonization and activation to develop its surface physical and chemical properties including surface area, pore volume and pore size. The CIH carbons were impregnated with a Pt precursor using an incipient wetness impregnation method. Dihydrogen hexachloroplanitic acid was used as a Pt precursor. Approximately 1 wt. % of Pt was directly loaded into the CIH carbon without further treatment. The Pt to carbon weight ratio was 0.01. The sample was dried in air at 120° C. overnight. After being calcined at 400° C. for 2 hours in inert gases, the sample was cooled down to room temperature and stored in air for future use. The Pt/C ratio of 0.01 was thus identical to commercial Pt/C catalysts in Examples VI and VII. The Pt/C ratio is a primary factor in determining Pt dispersion and chemical contact on carbon.

The inventive carbon monolith-supported Pt catalyst of Pt/CIH was ground into powders with the same particle size range as the commercial sample, and leached under the conditions described above. The reason for grinding carbon monolith-supported Pt catalysts into powder is to eliminate possible physical shape effects upon the basic leaching results. The result showed that there was 0.07 $\mu$g Pt/mL in the leaching solution. This indicates that there was very little Pt leachout in the basic solution for the carbon monolith-supported Pt/CIH catalyst. This result clearly demonstrates that the Pt is attached to carbon in a stable manner. This surprisingly good Pt stability probably results from strong chemical interaction between Pt and the carbon monolith surface introduced in catalyst preparation. For comparison, the integrated monolith Pt/CIH catalyst was also studied without further grinding and the Pt stability was similar to that of powdered samples.

EXAMPLE X

In-situ, carbon monolith-supported (in-situ Pt/C) catalysts were fabricated according to the method described in U.S. Pat. No. 5,488,023. Approximately 1 wt. % of Pt was loaded into the carbon in monolith. The Pt to carbon weight ratio was 0.01. The inventive, in-situ carbon monolith-supported Pt catalyst of Pt/C was ground into powders with the same particle size range as the commercial sample above, and then leached under the conditions described. The result showed 0.09 $\mu$g Pt/mL existing in solution for the in-situ Pt/C catalyst. This indicated that there was little Pt being dissolved in the basic solution for the in-situ Pt/C catalyst, similar to that of the Pt/CIH catalyst found in Example IX. It again suggested that the in-situ Pt/C catalyst was also much more stable in Pt on the carbon surface than are commercial counterparts of Pt/C and Pt/Al$_2$O$_3$ previously described.

Since the Pt catalyst was incorporated into the carbon body in the beginning of the process, it was anticipated that there would be intimate and strong chemical interaction between the Pt and the carbon surface introduced in the catalyst preparation. It was surprising to note that the in-situ Pt/C catalyst had very similar Pt leaching stability to the Pt/CIH catalyst described above. For comparison, the integrated, monolithic, in-situ Pt/C catalyst was also studied, and the obtained result of Pt stability was similar to that of the powdered samples.

The invention thus described has strong leaching-resistant, carbon monolith-supported catalysts with high performance, which are specially suitable for reactions under acidic conditions (pH ranging from 0 to 6.5) and severe basic conditions (pH ranging from 7.5 to 14).

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention as set further in the appended claims.

We claim:

1. In a method for promoting a catalytic reaction by contacting a liquid reactant mixture having a non-neutral pH, with a metallic catalyst supported upon a solid inorganic support, the improvement comprising: utilizing in said catalytic reaction a solid inorganic support including a honeycomb substrate having outer surfaces and pore surfaces, with pores extending into the substrate, and incorporating a substantially uninterrupted adherent layer of activated carbon over said outer surfaces and within said pore surfaces of said honeycomb substrate; and wherein said metallic catalyst is supported throughout said adherent layer of activated carbon.

2. The method in accordance with claim 1, wherein said solid inorganic support is further characterized as an extruded resin carbon honeycomb support.

3. The method in accordance with claim 1, wherein carbon is impregnated into said honeycomb substrate in the range of between approximately 5% and 99% by weight.

4. The method in accordance with claim 1, wherein said inorganic support has a pore volume in the approximate range of 0.1 to 1.4 Ml/g C.

5. The method in accordance with claim 1, wherein said inorganic support has a surface area in a range of between approximately 10 and 3,000 m$^2$/g C.

6. A method of promoting a catalytic reaction, comprising the steps of:
   a) providing a solid inorganic support including an inorganic honeycomb substrate having outer surfaces and pore surfaces, with pores extending into the substrate, and incorporating a substantially uninterrupted adherent layer of activated carbon over said outer surfaces and within said pore surfaces of the inorganic honeycomb substrate;
   b) supporting a metallic catalyst throughout said adherent layer of activated carbon; and
   c) contacting a liquid reactant mixture having a non-neutral pH with said metallic catalyst supported upon said solid inorganic support.

7. The method in accordance with claim 6, wherein said solid inorganic support of step (a) is further characterized as an extruded resin carbon honeycomb.

8. The method in accordance with claim 6, wherein said honeycomb substrate of step (a) is impregnated with carbon in the range of between approximately 5% and 99% by weight.

9. The method in accordance with claim 6, wherein said inorganic support of step (a) has a pore volume in the approximate range of 0.1 to 1.4 Ml/g C.

10. The method in accordance with claim 6, wherein said inorganic support of step (a) has a surface area in a range of between approximately 10 and 3,000 m$^2$/g C.

* * * * *